United States Patent [19]

Gillard et al.

[11] Patent Number: 5,017,597

[45] Date of Patent: May 21, 1991

[54] CYCLOHEPT(B)INDOLEALKANOIC ACIDS, PHARMACEUTICAL COMPOSITIONS AND USE

[75] Inventors: John W. Gillard, Baie d'Urfe; Yvan Guindon, Montreal; Howard E. Morton, Dollard Des Ormeaux; Yves Girard, Ile Bizard; Christiane Yoakim, Montreal, all of Canada

[73] Assignee: Merck Frosst Canada, Inc., Kirkland, Canada

[21] Appl. No.: 447,755

[22] Filed: Dec. 4, 1989

Related U.S. Application Data

[60] Division of Ser. No. 211,800, Jun. 27, 1988, Pat. No. 4,906,654, which is a continuation of Ser. No. 76,096, Jul. 21, 1987, Pat. No. 4,775,680.

[51] Int. Cl.$^5$ .................... A61K 31/40; C07D 209/86; C07D 209/88
[52] U.S. Cl. ................................. 514/411; 514/232.8; 514/253; 514/323; 514/381; 544/142; 544/372; 546/200; 548/252; 548/253; 548/439; 548/448
[58] Field of Search ................ 544/142, 372; 546/200; 548/252, 253, 439, 448; 514/232.8, 253, 323, 381, 411

[56] References Cited

U.S. PATENT DOCUMENTS 4,009,181  2/1977  Berger et al. .................... 548/448
4,057,559  11/1977  Asselin et al. .................... 548/439

OTHER PUBLICATIONS

Perni et al., *Chemical Abstracts*, vol. 98 (1983), 98: 16537q.

*Primary Examiner*—Robert W. Ramsuer
*Attorney, Agent, or Firm*—Gabriel Lopez; Joseph F. DiPrima

[57] ABSTRACT

Cyclohept[b]indolealkanoic acids and acid derivatives are disclosed. The compounds act as prostaglandin and thromboxane antagonists and are useful in treating asthma, diarrhea, hypertension, angina, platelet, aggregation, cerebral spasm, premature labor, spontaneous abortion, dysmenorrhea and nephrotoxicity caused by cyclosporin A and as cytoprotective agents.

10 Claims, No Drawings

CYCLOHEPT(B)INDOLEALKANOIC ACIDS, PHARMACEUTICAL COMPOSITIONS AND USE

CROSS REFERENCE

Division of Ser. No. 211,800, June 27, 1988, U.S. Pat. No. 4,906,654, which is a continuation of Ser. No. 76,096, July 21, 1987, U.S. Pat. No. 4,775,680.

U.S. Pat. No. 4,906,654 (Gillard et. al.) is incorporated herein by reference in its entirety.

DESCRIPTION OF THE INVENTION

The present invention relates to novel compounds of Formula I:

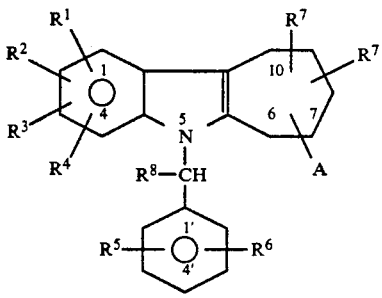

wherein:
A is $-(CR^9R^{10})_rR^{11}$;
$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) $-(CH_2)_nM$ wherein n is 0 to 3 and M is
  (a) $-C(O)R^{15}$;
  (b) $-C(O)NR^{17}R^{17}$;
  (c) $-CN$;
  (d) $-C(O)R^{16}$;
  (e) $-C(O)CH_2OH$ (hydroxymethyl ketone);
  (f) $-CF_3$;
  (g) $-R^{14}$;
  (h) -tetrazole;
  (i) $-OR^{12}$;
  (j) $-OC(O)R^{16}$;
  (k) $-OC(O)NR^{17}R^{17}$;
  (l) $-OC(O)OR^{18}$;
  (m) $-SR^{13}$;
  (n) $-S(O)R^{13}$;
  (o) $-S(O)_2R^{13}$;
  (p) $-S(O)_2NR^{17}R^{17}$;
  (q) $-NR^{17}R^{17}$;
  (r) $-NHC(O)R^{16}$;
  (s) $-NHS(O)_2R^{13}$;
  (t) $-N_3$;
  (u) $-NO_2$;
  (v) -halogen.
each $R^7$ is independently H or $C_1$ to $C_6$ alkyl;
each $R^8$ is independently H or $C_1$ to $C_6$ alkyl;
each $R^9$ is independently H or $C_1$ to $C_6$ alkyl;
each $R^{10}$ is independently H, OH, $C_1$ to $C_4$ alkoxy or $C_1$ to $C_4$ alkyl;
$R^{11}$ is $-C(O)OR^{19}$; $-C(O)R^{20}$; $CH_2OH$; $CHO$; tetrazole; $-C(O)NHS(O)_2R^{13}$; $NHS(O)_2R^{13}$; $-C(O)CH_2OH$; $-C(O)NR^{17}R^{17}$ or $NHS(O)_2OH$;
each $R^{12}$ is independently H; $C_1$ to $C_6$ alkyl; benzyl; or $R^{14}$;

each $R^{13}$ is independently $C_1$ to $C_6$ alkyl, $CF_3$ or $R^{14}$;
each $R^{14}$ is independently phenyl, mono-substituted phenyl, or di-substituted phenyl wherein the substituents are independently, $C_1$ to $C_3$ alkyl, $C_1$ to $C_3$ perfluoroalkyl, $C_1$ to $C_3$ alkoxy, halogen, CN, or $-C(O)OR^{15}$, or $-CH_2-C(O)OR^{15}$;
each $R^{15}$ is independently H, phenyl, benzyl or $C_1$ to $C_6$ alkyl;
each $R^{16}$ independently is H, $R^{13}$ or $(CH_2)_mC(O)OR^{15}$;
each $R^{17}$ is independently $R^{12}$, or two $R^{17}$ groups may be joined to form a 5 or 6 membered saturated ring optionally containing an oxygen atom or a second nitrogen atom, the latter being substituted by H or $C_1$ to $C_6$ alkyl;
each $R^{18}$ is independently $C_1$ to $C_6$ alkyl, benzyl or phenyl;
each $R^{19}$ is H, $C_1$ to $C_6$ alkyl, $R^{14}$, $R^{21}$ or $R^{22}$;
$R^{20}$ is $-(CH_2)_r-C(R^9)_2-(CH_2)_r-R^{23}$;
$R^{21}$ is $-CH_2-R^{14}$;
$R^{22}$ is $-CH_2-CH_2-R^{14}$
$R^{23}$ is (A) a monocyclic or bicyclic heterocyclic radical containing from 3 to 12 nuclear carbon atoms and 1 or 2 nuclear heteroatoms selected from N, S, or O and with each ring in the heterocyclic radical being formed of 5 to 6 atoms, or (B) the radical $W-R^{24}$;
$R^{24}$ contains up to 21 carbon atoms and is (1) a hydrocarbon radical or (2) an acyl radical of an organic acyclic or monocyclic carboxylic acid containing not more than 1 heteroatom in the ring;
W is O, S or NH;
m is 0 to 4
r is 0 to 6 and
t is 0 to 3.

What is claimed is:
1. A compound of the formula:

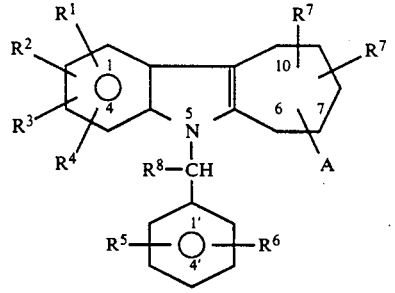

wherein:
A is $-(CR^9R^{10})_rR^{11}$;
$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) $-(CH_2)_nM$ wherein n is 0 to 3 and M is
  (a) $-C(O)R^{15}$;
  (b) $-C(O)NR^{12}R^{12}$;
  (c) $-CN$;
  (d) $-C(O)R^{16}$;
  (e) $-C(O)CH_2OH$ (hydroxymethyl ketone);
  (f) $-CF_3$;
  (g) $-R^{14}$;
  (h) -tetrazole;
  (i) $-OR^{12}$;
  (j) $-OC(O)R^{16}$;
  (k) $-OC(O)NR^{12}R^{12}$;

(l) —OC(O)OR$^{18}$;
(m) —SR$^{13}$;
(n) —S(O)R$^{13}$;
(o) —S(O)$_2$R$^{13}$;
(p) —S(O)$_2$NR$^{12}$R$^{12}$;
(q) —NR$^{12}$R$^{12}$;
(r) —NHC(O)R$^{16}$;
(s) —NHS(O)$_2$R$^{13}$;
(t) —N$_3$;
(u) —NO$_2$; or
(v) -halogen;

each R$^7$ is independently H or C$_1$ to C$_6$ alkyl;
each R$^8$ is independently H or C$_1$ to C$_6$ alkyl;
each R$^9$ is independently H or C$_1$ to C$_6$ alkyl;
each R$^{10}$ is independently H, OH, C$_1$ to C$_4$ alkoxy or C$_1$ to C$_4$ alkyl;
R$^{11}$ is —C(O)NHS(O)$_2$R$^{13}$;
each R$^{12}$ is independently H, C$_1$ to C$_6$ alkyl, benzyl, or R$^{14}$;
each R$^{13}$ is indepdendently C$_1$ to C$_6$ alkyl, CF$_3$, or R$^{14}$;
each R$^{14}$ is independently phenyl, mono-substituted phenyl, or di-substituted phenyl wherein the substituents are independently C$_1$ to C$_3$ alkyl, C$_1$ to C$_3$ perfluoroalkyl, C$_1$ to C$_3$ alkoxy, halogen, CN, —C(O)OR$^{15}$, or —CH$_2$—C(O)OR$^{15}$;
each R$^{15}$ is independently H, phenyl, benzyl, or C$_1$ to C$_6$ alkyl;
each R$^{16}$ independently is H, R$^{13}$, or (CH$_2$)$_m$C(O)OR$^{15}$;
each R$^{18}$ is independently C$_1$ to C$_6$ alkyl, benzyl, or phenyl;
m is 0 to 4;
r is 0 to 6; and
t is 0 to 3.

2. A compound of claim 1, wherein:
R$^1$, R$^2$, R$^3$, R$^4$, R$^5$ and R$^6$ are each independently selected from:
(1) hydrogen;
(2) alkyl having 1 to 6 carbon atoms;
(3) alkenyl having 2 to 6 carbon atoms;
(4) —(CH$_2$)$_n$M, wherein n is 0 or 1; and r is 1 to 6;

3. A compound of to claim 2, wherein:
A is attached to the 6- or 7- position;
n is 0; and
r is 1 or 2.

4. A compound of claim 3, wherein:
A is attached to the 6- or 7- position;
R$^1$, R$^2$, R$^3$ and R$^4$ are each independently selected from:
(1) hydrogen;
(2) alkyl having 1 to 6 carbon atoms;
(3) M, wherein M is
(a) —C(O)OR$^{15}$;
(b) —C(O)NR$^{12}$R$^{12}$;
(c) —CN;
(d) —C(O)R$^{16}$;
(f) —CF$_3$;
(h) -tetrazole;
(i) —OR$^{12}$;
(j) —OC(O)R$^{16}$;
(m) —SR$^{13}$;
(n) —S(O)R$^{13}$;
(o) —S(O)$_2$R$^{13}$;
(p) —S(O)$_2$NR$^{12}$R$^{12}$;
(t) —N$_3$; or
(v) -halogen;

R$^5$ and R$^6$ are independently selected from:
(1) hydrogen;
(2) alkyl having 1 to 6 carbon atoms;
(3) M, wherein M is
(a) —C(O)OR$^{15}$;
(b) —C(O)NR$^{12}$R$^{12}$;
(c) —CN;
(d) —C(O)R$^{16}$;
(f) —CF$_3$;
(h) -tetrazole;
(n) —S(O)R$^{13}$;
(o) —S(O)$_2$R$^{13}$;
(p) —S(O)$_2$NR$^{12}$R$^{12}$;
(t) —N$_3$;
(u) —NO$_2$; or
(v) -halogen;
each R$^{10}$ is independently H or C$_1$ to C$_4$ alkyl; and r is 1.

5. A compound of claim 1 of the formula:

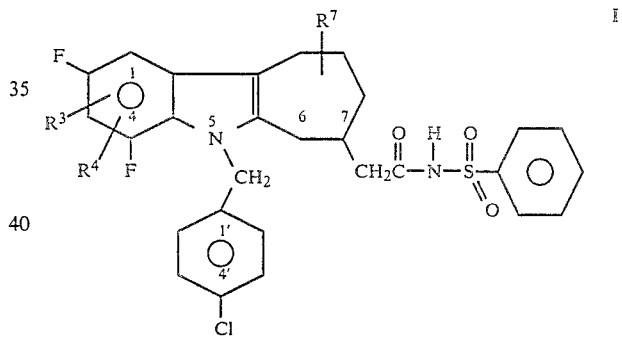

6. A compound of claim 1, which is a pure optical isomer.

7. A compound of claim 6, which is the (+)-isomer.

8. A compound of to claim 6, which is the (−)-isomer.

9. A method of inhibiting leukotriene synthesis in a mammal, which comprises administering to a mammal an effective amount of a compound of claim 1.

10. A pharmaceutical composition which comprises a compound of claim 1 and a pharmaceutically acceptable carrier.

* * * * *